(12) United States Patent
Zhang et al.

(10) Patent No.: US 12,364,402 B2
(45) Date of Patent: Jul. 22, 2025

(54) MULTI-MODAL SENSOR MODULE AND A MULTI-MODAL PHYSIOLOGICAL SIGNAL MONITORING SYSTEM

(71) Applicant: Hong Kong Centre for Cerebro-Cardiovascular Health Engineering Limited, Hong Kong (HK)

(72) Inventors: Yuanting Zhang, Hong Kong (HK); Zijun Liu, Hong Kong (HK); Ting Xiang, Hong Kong (HK); Nan Ji, Hong Kong (HK)

(73) Assignee: Hong Centre For Cerebro-Cardiovascular Health Engineering Limited, Hong Kong (HK)

( * ) Notice: Subject to any disclaimer, the term of this patent is extended or adjusted under 35 U.S.C. 154(b) by 437 days.

(21) Appl. No.: 17/972,952

(22) Filed: Oct. 25, 2022

(65) Prior Publication Data

US 2023/0380700 A1    Nov. 30, 2023

(30) Foreign Application Priority Data

May 26, 2022 (CN) .......................... 202221308988.4

(51) Int. Cl.
*A61B 5/02* (2006.01)
*A61B 5/0205* (2006.01)
(Continued)

(52) U.S. Cl.
CPC ...... *A61B 5/02055* (2013.01); *A61B 5/02427* (2013.01); *A61B 5/0531* (2013.01);
(Continued)

(58) Field of Classification Search
None
See application file for complete search history.

(56) References Cited

U.S. PATENT DOCUMENTS

2017/0366213 A1* 12/2017 Camacho Perez ........................ A61B 5/02055
2021/0212606 A1* 7/2021 Tran ..................... A61B 5/0024

* cited by examiner

*Primary Examiner* — Ankit D Tejani
(74) *Attorney, Agent, or Firm* — GableGotwals (57) ABSTRACT

The present invention relates to a multi-modal sensor module, comprising an electrode base, an insulating film sheet, a functional layer and a protective film; the protective film is used for isolating external environment with a side away from the functional layer for use in contacting surface of biological tissues; the functional layer comprises a substrate and at least one sensor module provided in isolation in the substrate; a side of the electrode base away from the insulating film sheet is used for contacting surface of the biological tissues; the multi-modal sensor module is in a state of collecting electrocardiogram (ECG) signal, a side of the protective film away from the functional layer and a side of the electrode base away from the insulating film sheet are both for contacting surface of the biological tissues, so that the protective film, the biological tissues and the electrode base form an ECG signal collection path. The present invention integrates each sensor module in the same functional layer for measuring various physiological signals or estimating arterial blood pressure, and the use of the electrode base and the protective film coordinates collection of the ECG signal of the biological tissues. The design is clever and the structure of the multi-modal sensor module is simplified.

8 Claims, 7 Drawing Sheets

(51) Int. Cl.
*A61B 5/024* (2006.01)
*A61B 5/0531* (2021.01)
*A61B 5/256* (2021.01)

(52) U.S. Cl.
CPC ...... *A61B 5/256* (2021.01); *A61B 2562/0209* (2013.01); *A61B 2562/0219* (2013.01); *A61B 2562/0271* (2013.01)

MULTI-MODAL SENSOR MODULE AND A MULTI-MODAL PHYSIOLOGICAL SIGNAL MONITORING SYSTEM

CROSS-REFERENCE TO RELATED APPLICATIONS

This United States application claims priority to Chinese Patent Application No. 202221308988.4 filed 26 May 2022 which is incorporated herein by reference.

FIELD OF THE INVENTION

The present invention relates to the technical field of physiological signal monitoring, specifically, this application relates to a multi-modal sensor module and a multi-modal physiological signal monitoring system.

BACKGROUND OF THE INVENTION

With the vigorous development of science and technology, people's living standard is improving, and they pay more and more attention to the physiological health condition of biological tissues (human or other animals, etc.). Therefore, to manage health conditions, daily monitoring of physiological signals of biological tissues is needed to obtain real-time physiological alerts of biological tissues' bodies in everyday life. And to seek timely medical consultation when abnormal physiological signals occur, which is conducive to an early screening of diseases that the biological tissues may suffer from and gives excellent protection to the health conditions of biological tissues.

Currently, most physiological signal monitoring systems use many kinds of sensors to collect physiological signals of biological tissues, then analyze and process the collected signals to derive the monitoring results of the physiological signals. Finally, conduct the corresponding processing (e.g., consultation) according to the monitoring results.

However, more physiological signals need to be collected to understand the physiological health of biological tissues fully. Unavoidably, a correspondingly large number of sensors are used, making it challenging to monitor the physiological signs of biological tissues daily.

OBJECTS OF THE INVENTION

An object of the present invention is to provide a multi-modal sensor module and a multi-modal physiological signal monitoring system.

The above object is met by the combination of features of the main claims; the sub-claims disclose further advantageous embodiments of the invention.

One skilled in the art will derive from the following description other objects of the invention. Therefore, the foregoing statements of object are not exhaustive and serve merely to illustrate some of the many objects of the present invention.

SUMMARY OF THE INVENTION

This present application relates to a multi-modal sensor module and a multi-modal physiological signal monitoring system to address the technical problem of the existing technology that there are many types of sensors, and hard to realize daily real-time monitoring of physiological signals of biological tissues.

In the first aspect, this application proposes a multi-modal sensor module, comprising an electrode base, an insulating film sheet, a functional layer, and a protective film;
  the protective film is for use in isolating external environment and a side of the protective film away from the functional layer is for use in contacting surface of biological tissues, the protective film is of an opaque material;
  the functional layer comprises a substrate and at least one sensor module provided in isolation in the substrate; the electrode base, the insulating film sheet, the substrate, and the protective film are in a stacked arrangement; the sensor module is for use in acquiring at least one physiological signal or arterial blood pressure estimation of the biological tissues;
  a side of the electrode base away from the insulating film sheet is for use in contacting surface of the biological tissues, the insulating film sheet and the electrode base are both of transparent materials;
  the multi-modal sensor module is in a state of collecting ECG signal, a side of the protective film away from the functional layer and a side of the electrode base away from the insulating film sheet are both for use in contacting surface of the biological tissues, so that the protective film, the biological tissues, and the electrode base form an ECG signal collection path.

Optionally, the sensor module includes: an ultrasonic sensor module; the ultrasonic sensor module comprises a plurality of piezoresistors arranged in an array;
  a side of the piezoresistors is arranged to face the protective film, and another side passes through the insulating film sheet and the electrode base for contacting surface of the biological tissues;
  a first portion of the piezoresistors is annularly distributed at an edge region of the substrate, a second portion of the piezoresistors is positioned at a center region of the substrate.

Optionally, the sensor module further comprises a pressure sensor and an accelerometer;
  the pressure sensor and the accelerometer are positioned between the first portion of the piezoresistors and the second portion of the piezoresistors.

Optionally, the sensor module further comprises a first PPG sensor module; the first PPG sensor module comprises a light source, an optical barrier and a first photodetector arranged in interval in sequence;
  the light source, the optical barrier and the first photodetector are all positioned between the first portion of the piezoresistors and the second portion of the piezoresistors, the light source corresponds with the pressure sensor, and the first photodetector is positioned parallel to the accelerometer.

Optionally, the light source comprises at least one monochromatic light source.

Optionally, the sensor module further comprises a second PPG sensor module;
  the second PPG sensor module comprises at least two light sources and a second photodetector;
  at least two light sources are evenly distributed at a periphery of the second photodetector.

Optionally, multi-modal sensor module further comprising a first temperature sensor module, a first wristband and a first bioimpedance sensor module;
  the first temperature sensor module surrounds a periphery of the electrode base, the first bioimpedance sensor module is provided at a side of the first wristband facing the biological tissues.

Optionally, multi-modal sensor module further comprises a second wristband, a second temperature sensor module and a second bioimpedance sensor module:

two ends of the second wristband are respectively connected with two ends of the electrode base;

the second temperature sensor module is positioned at a side of the second wristband facing the biological tissues, the second bioimpedance sensor module is connected with the electrode base.

Optionally, the second bioimpedance sensor module comprises two voltage detecting electrode sheets and two electric current supplying electrode sheets;

the electrode base comprises four holes;

the two voltage detecting electrode sheets and the two electric current supplying electrode sheets are respectively embedded in the four holes, a side of the voltage detecting electrode sheets and the electric current supplying electrode sheets away from the protective film being flush with a side of the electrode base away from the insulating film sheet.

In a second aspect, the present invention provides a multi-modal physiological signal monitoring system comprising any one of the multi-modal sensor modules as provided in the first aspect above.

The technical solutions provided by embodiments of the present application bring beneficial technical effects including:

the multi-modal sensor module is equipped with the capability to acquire multiple physiological signals simultaneously. The multi-modal sensor module includes an electrode base, an insulating film sheet, a functional layer, and a protective film. Multi-sensor components are integrated in the same functional layer and share the same protective film and electrode base, resulting in a compact and compact structure with a small footprint. The electrode base and protective film of this application embodiment can be equivalent to a cardiac electrode sheet that can form a direct pathway with biological tissue to collect the cardiac signal from the biological tissue, eliminating the need for a conventional substrate and protective layer and reducing the number of layers in the multi-modal sensor module. The insulation film can isolate the substrate of the functional layer and the electrode base's substrate to avoid electromagnetic interference between the functional layer and the electrode base. The insulation film is thinner than the electrode base, which has less impact on the thickness of the entire multi-modal sensor module. The protective film protects the electrode base, the insulation film, and the functional layer placed under the protective film from the external environment. Additional aspects and advantages of the present application will be given in part in the following description, which will become apparent from the following description or the practice of the present invention.

BRIEF DESCRIPTION OF THE DRAWINGS

The above-described and/or additional aspects and advantages of the present application will become apparent and readily understood from the following description of embodiments in conjunction with the accompanying drawings.

DESCRIPTION OF PREFERRED EMBODIMENTS

Embodiments of the present invention are described in connection with the following figures in the present invention. It should be understood that the embodiments set forth below in conjunction with the accompanying figures are exemplary descriptions to explain the technical solutions of the embodiments of the present invention and do not constitute a limitation of the technical solutions of the embodiments of the present invention.

It will be understood by technicians in the art unless expressly stated, the singular forms "one," "a". "said," and "the" as used herein "may also include the plural form. It should be understood that when we refer to a component being "connected" or "coupled" to another element, the one component may be directly connected or coupled to the other component, or it may refer to the one component and the other component being connected through an intermediate component. The term "and/or" as used herein refers to at least one of the items defined by the term; for example. "A and/or B" may be implemented as "A," or as "B," or "A and B."

In order to make the purpose, technical solutions and advantages of this application clearer, the following will be described in further detail in conjunction with the accompanying figures for the implementation of this application.

The development idea of this application includes: Generally, in the physiological signal monitoring system, multiple sensor components are posited on the surface of biological tissues to collect each physiological signal of biological tissues and then transmit it to the signal analysis and processing module for analysis and processing, this design circuit connection is complicated, the sensor components occupy ample space, wear cumbersome, and make the measured biological tissues discomfort, and it is challenging to realize daily real-time monitoring of physiological signals of biological tissues.

The present application provides a multi-modal sensor module and a multi-modal physiological signal monitoring system designed to solve the technical problems of the prior art described above.

The technical solutions of the present application and how the technical solutions of the present application solve the above technical problems are described in detail below with specific embodiments. It should be noted that the following embodiments can be cross-referenced, borrowed, or combined, and the description of the same terms, features, implementation steps, etc., in different embodiments will not be repeated.

Figure 1:
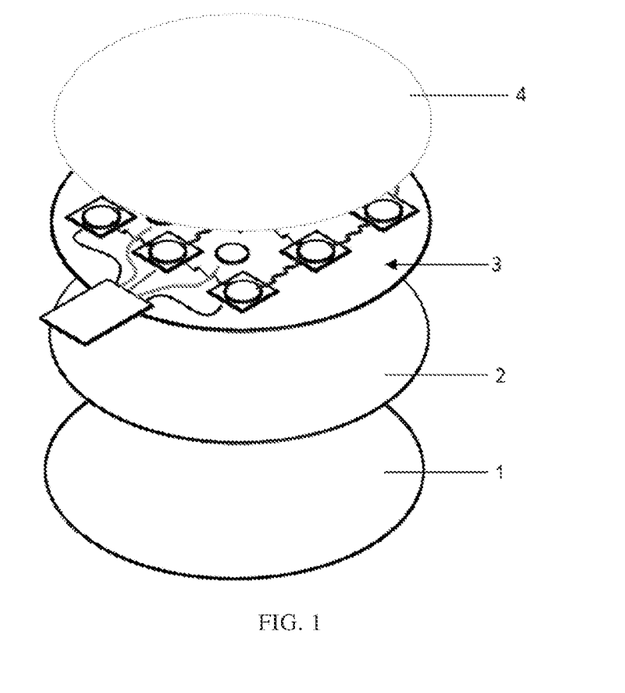
FIG. 1 shows a schematic diagram of the structure of a multi-modal sensor module provided by an embodiment of the present invention.

Referring to FIG. 1, embodiments of the present invention provide a multi-modal sensor module 100 comprising: an electrode base 1, an insulating film sheet 2, a functional layer 3, and a protective film 4.

The protective film 4 is for use in isolating external environment and a side of the protective film away from the functional layer 3 is for use in contacting surface of biological tissues, the protective film 4 is of an opaque material;

the functional layer 3 comprises a substrate 31 and at least one sensor module provided in isolation in the substrate 31; the electrode base 1, the insulating film sheet 2, the substrate 31 and the protective film 4 are in a stacked arrangement; the sensor module 32 is for use in acquiring at least one physiological signal or arterial blood pressure estimation of the biological tissues, a side of the electrode base 1 away from the insulating film sheet 2 is for use in contacting surface of the biological tissues, the insulating film sheet 2 and the electrode base 1 are both of transparent materials;

the multi-modal sensor module 100 is in a state of collecting ECG signal, a side of the protective film 4 away from the functional layer 3 and a side of the electrode base 1 away from the insulating film sheet 2 are both for use in contacting surface of the biological tissues, so that the protective film 4, the biological tissues and the electrode base 1 form an ECG signal collection path.

Multi-modal refers to the data of multiple analog states collected by different sensors, such as various physiological signals of biological tissues. The multi-modal study is about the fusion of these different modalities of data. The multi-modal sensor module 100 includes, but is not limited to, a device integrated design and a structural fusion design. The device integrated design is to incorporate multiple sensor modules 32 in the same signal sensor, while the structural fusion design is to incorporate multiple sensor modules 32 in one functional layer 3 with the same protective film 4 and the same substrate, which is streamlined and compact, and easier to integrate into other wearable products as a physiological signal monitoring module to achieve simultaneous acquisition of multiple physiological signals or arterial blood pressure estimation.

Figure 6:
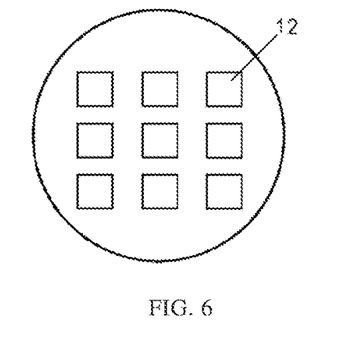
FIG. 6 shows a schematic diagram of the structure of an electrode base of a multi-modal sensor module provided in an embodiment of the present invention.
Figure 7:
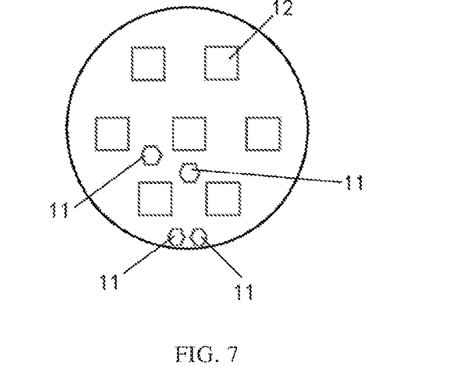
FIG. 7 shows a schematic diagram of the structure of an electrode base of another multi-modal sensor module provided by an embodiment of the present application.

In this embodiment, the multi-modal sensor module 100 has the function of acquiring multiple physiological signals simultaneously. The multi-modal sensor module 100 includes an electrode base 1, an insulating film sheet 2, a functional layer 3 and a protective film 4, with multiple sensor components 32 integrated with the same functional layer 3 and sharing the same protective film 4 and electrode base 1, with a streamlined and compact structure that takes up little space. The electrode base 1 and protective film 4 of this application embodiment can be equivalent to an ECG electrode sheet, which can directly form a pathway with biological tissues to collect ECG signals from biological tissues without using a traditional base and protective layers, reducing the number of layers of multi-modal sensor module 100. The insulating film sheet 2 isolates the substrate 31 of the functional layer 3 from the electrode base 1 to avoid electromagnetic interference between the functional layer 3 and the electrode base 1, and the insulating film sheet 2 is thinner compared to the electrode base 1, which has less impact on the thickness of the entire multi-modal sensor module 100. The protective film 4 can protect the electrode base 1, the insulating film sheet 2, and the functional layer 3 placed under the protective film 4 from the external environment. Referring to FIGS. 6 and 7, electrode base 1 has some skeleton 12 through which the piezoelectric resistor can pass to contact with the biological tissue surface.

For example, the biological tissue is the user, and the multi-modal sensor module 100 provided in this application is similar to a dial that can be worn on the wrist of the user, with the bottom of the dial being the electrode base 1 in direct contact with the skin and the protective film 4 at the topmost layer, and when the other hand of the user touches the protective film 4, the electrode base 1 and the protective film 4 can be equivalent to a cardiac electrode piece that can form a direct pathway with the user to collect the user's ECG signal.

Understandably, the biological tissue surface described in this application includes, but is not limited to, human skin.

Optionally, one side of the substrate 31 is connected to the insulating film sheet 2, and the other side is provided with each sensor assembly 32.

Figure 2:
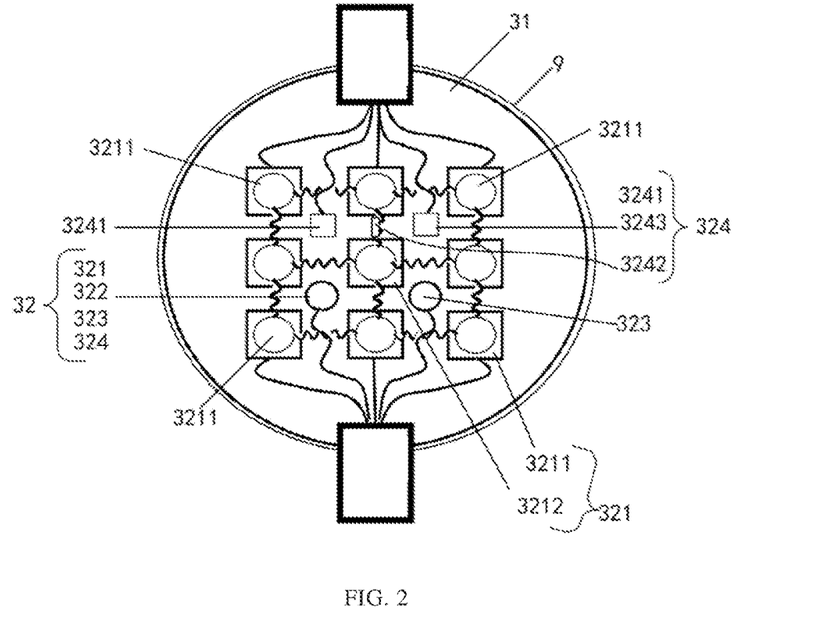
FIG. 2 shows a schematic diagram of the structure of the functional layer of a multi-modal sensor module provided by an embodiment of the present application.
Figure 5:
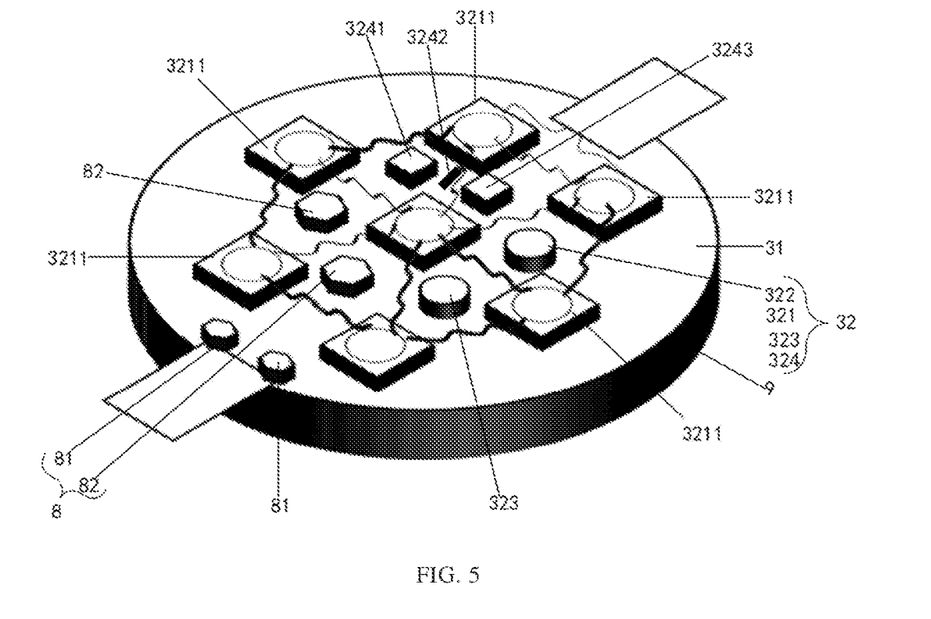
FIG. 5 shows a schematic diagram of the structure of the functional layer and the second bioimpedance sensor assembly connected to another multi-modal sensor module provided by an embodiment of the present invention.

In some possible embodiments, referring to FIGS. 2 and 5, the sensor assembly 32 includes: an ultrasonic sensor assembly 321, the ultrasonic sensor assembly 321 includes a plurality of piezoelectric resistors arranged in an array.

One side of the piezoelectric resistors is oriented toward the protective film 4 and the other side passes through the spacer film sheet 2 and the electrode base 1 and is used to contact the surface of the biological tissue.

The first part of the piezoelectric resistors 3211 are distributed in a ring shape in the edge region of the substrate 31, and the second part of the piezoelectric resistors 3212 are in the middle region of the substrate 31.

In this embodiment, a plurality of piezoelectric resistor arrays are arranged on the substrate 31, divided into a first part and a second part, wherein the first part piezoelectric resistor 3211 is distributed in a ring shape and can be used to detect noise, and the second part piezoelectric resistor 3212 is centered and can be used to detect blood pulsation signals. Thus, the entire ultrasonic sensor assembly 321 can achieve simultaneous acquisition of noise signals and blood pulsation signals.

Optionally, the ultrasound sensor assembly 321 may also include a plurality of ultrasound sensors, with the plurality of ultrasound sensor arrays arranged on the substrate 31.

Optionally, the number of the plurality of piezoelectric resistors 3211 may be set as appropriate, including, but not limited to, six, eight, or ten and more.

Optionally, referring to FIG. 2, the number of the first portion piezoelectric resistors 3211 is 8, distributed in a rectangle, and the number of the second portion piezoelectric resistors 3212 is 1, placed in the middle of the rectangle.

Optionally, referring to FIG. 5, the number of piezoelectric resistors 3211 in the first part is 6, distributed in a hexagonal shape, and the number of piezoelectric resistors 3212 in the second part is 1, placed in the middle of the hexagon.

In some possible embodiments, refer to FIG. 2 and FIG. 5, the sensor assembly 32 also includes: a pressure sensor 322 and an accelerometer 323.

The pressure sensor 322 and accelerometer 323 are located between the first portion piezoelectric resistor 3211 and the second portion piezoelectric resistor 3212.

In this embodiment, the piezoelectric resistor array is arranged with gaps between the piezoelectric resistors, and the pressure sensor 322 and the accelerometer 323 can be positioned in the holes of the piezoelectric resistors for acquiring pressure signals and acceleration signals, respectively, and using the pressure sensor 322 to monitor the external pressure for self-calibration.

Optionally, the pressure sensor 322 and the accelerometer 323 both have a two-layer structure of a sensing layer and a receiving layer, which can be used to obtain pressure signals and acceleration signals through changes in the distance between the upper and lower substrate 31, and thus the pressure magnitude or height changes of the measured part. The sensing and receiving layers are embedded in the substrate 31.

Optionally, due to the similarity in structural design as well as materials of accelerometer 323 and pressure sensor 322, the two can be fused and integrated into a mechanical sensing device with a pressure sensing function as well as an acceleration change monitoring function, interspersed in substrate 31.

In some possible embodiments, refer to FIG. 2, the sensor assembly 32 further includes: a first PPG sensor module 324, the first PPG sensor module 324 includes a light source 3241, an optical barrier 3242, and a first photodetector 3243 disposed sequentially at intervals.

Light source 3241, optical barrier 3242 and the first photodetector 3243 are located between the first part of the piezoelectric resistor 3211 and the second part of the piezoelectric resistor 3212.

The light source 3241 is provided in correspondence with the pressure sensor 322, and the first photodetector 3243 is provided in correspondence with the accelerometer 323.

In this embodiment, the light source 3241 and the first photodetector 3243 are interspersed and distributed in the piezoelectric resistance gap, which makes reasonable use of the space on the substrate 31 and skillfully integrates multiple sensor components 32 in one to obtain the multi-modal sensor module 100, which can collect multiple physiological signals simultaneously.

Optionally, the light source 3241, the optical barrier 3242 and the first photodetector 3243 are provided side-by-side. The optical barrier 3242 is located between the light source 3241 and the first photodetector 3243.

Optionally, when the ultrasonic sensor assembly 321 is squarely distributed, the first portion of the piezoelectric resistor 3211 and the second portion of the piezoelectric resistor 3212 also have a rectangular gap between them, in which the light source 3241, the first photodetector 3243, the pressure sensor 322, and the accelerometer 323 are evenly distributed for easy alignment. For example, the light source 3241, the first photodetector 3243, the pressure sensor 322, and the accelerometer 323 are provided at each of the four corners of the rectangular slit or are set correspondingly on the symmetrical axis of the rectangular slit.

In some possible embodiments, the light source 3241 includes at least one monochromatic light source 3241.

The monochromatic light source 3241 in this embodiment may be a light emitting diode that emits light of only one wavelength, and the number of light emitting diodes may be one or more.

Figure 9:
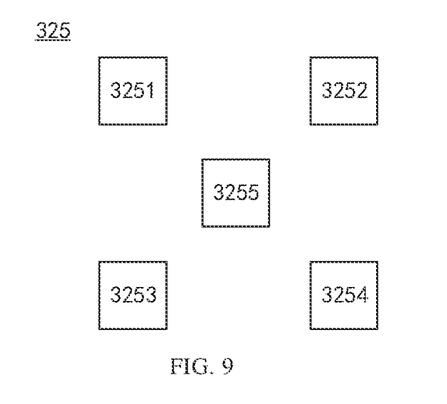
FIG. 9 shows a schematic diagram of the structure of a second PPG sensor assembly of a multi-modal sensor module provided by an embodiment of the present invention.

In some possible embodiments, refer to FIG. 9, the sensor assembly 32 further includes: a second PPG sensor assembly 325.

The second PPG sensor assembly 325 includes: at least two light sources and a second photodetector 3255.

At least two light sources are uniformly distributed around the periphery of said second photodetector 3255. In this embodiment, multi-wavelength PPG sensor technology is used. Light sources of different wavelengths are evenly distributed around the second photodetector 3255 in a centered arrangement, and the design is also suitable for various combinations of several multi-wavelength PPG sensors. The light sources and photodetectors capable of emitting various colors of light are distributed interspersed in the gaps of the piezoelectric resistors, which are not in contact with each other and spatially separated from the piezoelectric resistors or other sensor assemblies 32 and are able to avoid interactions between the various sensor assemblies 32.

Optionally, the second PPG sensor assembly 325 includes: red LED 3251, blue LED 3252, green LED 3253, yellow LED 3254, and second photodetector 3255.

Red LED 3251, blue LED 3252, green LED 3253, yellow LED 3254 uniformly distributed around the second photodetector 3255.

Optionally, the functional layer 3 of the multi-modal sensor module 100 provided in the present application, in which the sensor assemblies 32 are separated from each other, may be separated using solid state ultrasound and sensing hydrogel layers.

Optionally, referring to FIG. 5, when the ultrasound sensor assembly 321 is distributed in a hexagonal shape, the light source 3241, the first photodetector 3243, the pressure sensor 322, the accelerometer 323, and the two electric current supplying electrode sheets 82 are also uniformly distributed in a hexagonal shape to facilitate alignment.

Optionally, light in both the first PPG sensor assembly 324 and the second PPG sensor assembly 325 can reach the skin surface through the transparent insulating film sheet 2 and the electrode base 1 to act as a detection signal.

Figure 3:
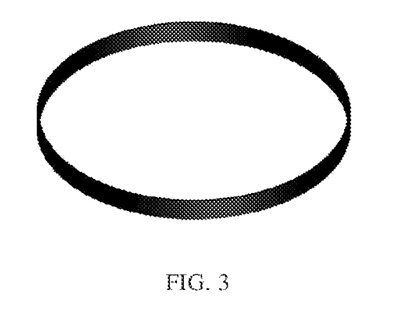
FIG. 3 shows a schematic diagram of the structure of a first temperature sensor assembly of a multi-modal sensor module provided in an embodiment of the present invention.
Figure 4:
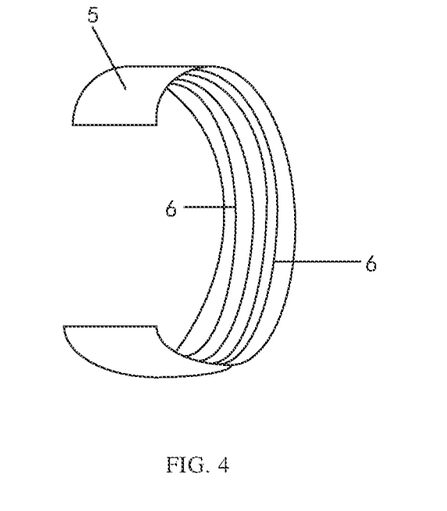
FIG. 4 shows a schematic diagram of the structure of a first wristband and a first bioimpedance sensor assembly connected to a multi-modal sensor module provided in an embodiment of the present invention.

In some possible implementations, refer to FIGS. 2, 3 and 4, the multi-modal sensor module 100 also includes a first temperature sensor assembly 9, a first wrist strap 5 and a first bioimpedance sensor assembly 6.

The first temperature sensor assembly 9 surrounds the periphery of the electrode base 1, and the first bioimpedance sensor assembly 6 is provided on the side of the first wristband 5 facing the biological tissue.

In this embodiment, the laminated structure of the multi-modal sensor module 100 can be regarded as a dial, such as the laminated electrode base 1, an insulating film sheet 2, the functional layer 3 and the protective film 4 forming the dial, and the multi-modal sensor module 100 also includes the first wristband 5, which is connected to the dial to form a watch-like wearable device, and is easy to wear on the human wrist to achieve daily and real-time monitoring of the human physiological signal or arterial blood pressure estimation.

Among them, the temperature signal is important among the physiological signals, and the temperature sensor needs to be in direct contact with the skin when measuring the temperature. In this embodiment, since the electrode base 1 acts as a cardiac electrode piece in direct contact with the skin, when the first temperature sensor assembly 9 is integrated in the dial position, it is designed to be on the peripheral edge of the electrode base 1. When the wearable watch is worn on the wrist, the electrode base 1 is in direct contact with the skin, and the first temperature sensor assembly 9 surrounding the electrode base 1 is also in contact with the skin, facilitating the acquisition of the skin temperature signal.

In this embodiment, the first bioimpedance sensor assembly 6 can be placed on the inner side of the first wristband 5, towards the wrist, and therefore can fit the skin of the wrist.

Optionally, referring to FIG. 4, the first bioimpedance sensor assembly 6 includes four electrodes, and the four electrodes are distributed on the wristband at a certain spacing to achieve uniform tissue current excitation, eliminating the problem of inaccurate voltage monitoring due to transmission of the current signal from point to point.

Optionally, the first temperature sensor assembly 9 may adopt a flexible thin film temperature sensor structure.

In some possible implementations, refer to FIGS. 5-FIG. 9, the multi-modal sensor module 100 further includes a second wrist strap 7, a second temperature sensor assembly 10, and a second bioimpedance sensor assembly 8.

Figure 8:
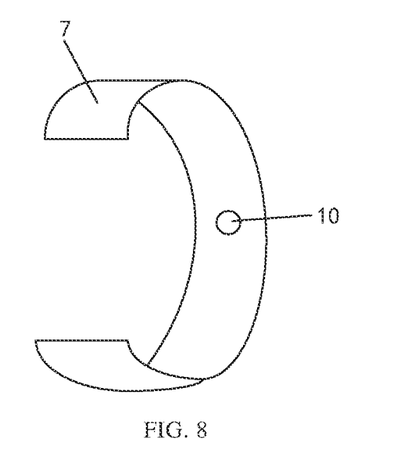
FIG. 8 shows a schematic diagram of the structure of a second wristband and a second temperature sensor assembly connected to a multi-modal sensor module provided in an embodiment of the present application.

The ends of the second wrist strap 7 are connected to the ends of the electrode base 1, respectively.

The second temperature sensor assembly 10 is located on the side of the second wristband 7 toward the biological tissue, and the second bioimpedance sensor assembly 8 is coupled to the electrode base 1.

In this embodiment, a second wristband 7 is provided, and unlike the first wristband 5, the second temperature sensor assembly 10 is provided on the inner side of the second wristband 7, toward the wrist, and is also capable of directly contacting the skin of the wrist to collect the temperature signal of the skin. To avoid interference with the second temperature sensor assembly 10, the second bioimpedance sensor assembly 8 is provided on the dial, making reasonable use of the space of the dial.

In some possible embodiments, the second bioimpedance sensor assembly 8 comprises two voltage detecting electrode sheets 81 and two electric current supplying electrode sheets 82. The electrode base 1 has four holes 11, the two voltage detecting electrode sheets 81 and the two electric current supplying electrode sheets 82 are embedded in each of the four holes 11, with the voltage detecting electrode sheets 81 and the electric current supplying electrode sheets 82 on the side away from the protective film 4 flush with the side of the electrode base 1 is flush with the side of the electrode base 1 that is away from the electrical insulation film 2.

The two electric current supplying electrode sheets 82 in this embodiment are used to supply an applied current, and after the current flows through the body, it is detected using two voltage detecting electrode sheets 81 to collect bioimpedance signals. Referring to FIG. 7, the electrode base in FIG. 7 has a through-hole 11.

Figure 10:
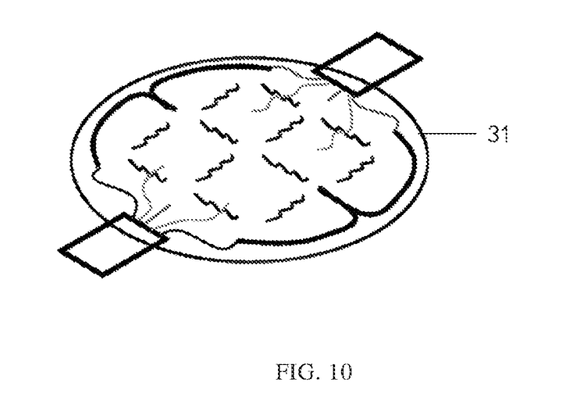
FIG. 10 shows a schematic diagram of the alignment structure of the functional layer of a multi-modal sensor module provided in this application embodiment.

Optionally, referring to FIG. 10, the multi-modal sensor module 100 also has a row of wires, the row of wires being provided at opposite ends of the substrate 31, capable of storing and enveloping the wires inside the dial. Two electric current supplying electrode sheets 82 are provided between the first portion piezoelectric resistor 3211 and the second portion piezoelectric resistor 3212, and two voltage detecting electrode sheets 81 are provided at one end of the substrate 31 having the alignment lines to facilitate the alignment lines.

In a second aspect, the present application provides a multi-modal physiological signal monitoring system comprising: any of the multi-modal sensor modules 100 as provided in the first preceding aspect.

This embodiment uses any of the multi-modal sensor modules 100 provided in the preceding embodiments, which are similar in implementation and will not be described here. This embodiment uses the multi-modal sensor module 100 to acquire various physiological signals or arterial blood pressure estimates and then processes and fuses multiple physiological signals containing blood pressure information through a signal processing analysis system to obtain rich and accurate multiple physiological data, such as ECG information, blood oxygen saturation or blood pressure information, etc. The blood pressure information includes, but is not limited to, continuous and beat-to-beat blood pressure information.

The application of embodiments of the present invention is capable of achieving at least the following beneficial effects:

1. The multi-modal sensor module 100 has the function of simultaneously acquiring multiple physiological signals or arterial blood pressure estimation. The multi-modal sensor module 100 includes an electrode base 1, an insulating film sheet 2, a functional layer 3, and a protective film 4, with multiple sensor components 32 integrated with the same functional layer 3 and sharing the same protective film 4 and electrode base 1, with a streamlined and compact structure and small space occupation. The electrode base 1 and protective film 4 of this application embodiment can be equivalent to the ECG electrode sheet, which can directly form a pathway with biological tissues to collect ECG signals from biological tissues without using the traditional substrate and protective layer, reducing the number of layers of the multi-modal sensor module 100. The spacer film 2 isolates the substrate 31 of the functional layer 3 from the electrode base 1 to avoid electromagnetic interference between the functional layer 3 and the electrode base 1, and the spacer film 2 is thinner than the electrode base 1, which has less impact on the thickness of the entire multi-modal sensor module 100. The protective film 4 can protect the electrode base 1, the isolation film sheet 2, and the functional layer 3 from the external environment under the protective film 4.

2. A plurality of piezoelectric resistor arrays are arranged on the substrate 31 and divided into a first part and a second part, wherein the first part of the piezoelectric resistors 3211 are distributed in a ring shape and can be used to detect noise, and the second part of the piezoelectric resistors 3212 are centered and can be used to detect the blood pulsation signal. Thus, the entire ultrasonic sensor assembly 321 can simultaneously acquire noise signals and blood pulsation signals.

3. The piezoelectric resistor array is arranged with gaps between the piezoelectric resistors, and the pressure sensor 322 and the accelerometer 323 can be set in the holes of the piezoelectric resistors for obtaining pressure signals and acceleration signals, respectively, and using the pressure sensor 322 to monitor the external pressure for self-calibration.

4. Multi-wavelength PPG sensor technology is used. Light sources 3241 of different wavelengths are evenly distributed around the second photodetector 3255 in a centered arrangement. The design is also suitable for various combinations of multi-wavelength PPG sensors. The light sources 3241 and photodetectors capable of emitting multiple colors of light are distributed interspersed in the gaps of the piezoelectric resistors, which are not in contact with each other and are spatially separated from the piezoelectric resistors or other sensor assemblies 32, and can avoid interactions between the various sensor assemblies 32.

5. The first bioimpedance sensor assembly 6 can be placed on the inner side of the first wristband 5, toward the wrist, and therefore can fit the skin of the wrist. The first bioimpedance sensor assembly 6 includes four electrodes, and the four electrodes are distributed on the wristband at a certain spacing to achieve uniform tissue current excitation, eliminating the problem of inaccurate voltage monitoring due to transmission of the current signal from point to point.

In the description of this application, the words "center", "top", "bottom", "front", "back", "left", "right", "vertical", "horizontal", "top". "bottom", "inside", "outside", etc. indicate an orientation or positional relationship based on the exemplary orientation or positional relationship shown in the accompanying drawings and are intended to facilitate or simplify the description of embodiments of this application, not to indicate or imply that the device or component referred to must have a particular orientation, be constructed and operate in a particular orientation, and therefore are not to be construed as limiting the application.

The terms "first" and "second" are used for descriptive purposes only, and are not to be construed as indicating or implying relative importance or implicitly specifying the number of technical features indicated. Thus, features qualified with "first" and "second" may explicitly or implicitly include one or more such features. In the description of this application, unless otherwise specified, "plurality" means two or more.

In the description of this application, it is to be noted that unless otherwise expressly specified and limited, the terms "mounted," "connected," and "connected" are to be understood in a broad sense, e.g., they may be, for example, it can be a fixed connection, a removable connection, or a one-piece connection; it can be a direct connection or an indirect connection through an intermediate medium, and it can be a connection within two components. To a person of ordinary skill in the art, the specific meaning of the above terms in the context of this application can be understood on a case-by-case basis.

In the description of this specification, specific features, structures, materials, or characteristics may be combined appropriately in any embodiments or examples.

The above description is only part of the implementation of this application. It should be noted that for a person of ordinary skill in the art, without departing from the technical conception of the scheme of this application, the use of other similar means of implementation based on the technical ideas of this application also falls within the scope of protection of the embodiments of this application.

The invention claimed is:

1. A multi-modal sensor module, comprising an electrode base, an insulating film sheet, a functional layer and a protective film;
    the protective film is for use in isolating external environment and a side of the protective film away from the functional layer is for use in contacting surface of biological tissues, the protective film is of an opaque material;
    the functional layer comprises a substrate and at least one sensor module provided in isolation in the substrate; the electrode base, the insulating film sheet, the substrate, and the protective film are in a stacked arrangement; the sensor module is for use in acquiring at least one physiological signal or arterial blood pressure estimation of the biological tissues;
    a side of the electrode base away from the insulating film sheet is for use in contacting surface of the biological tissues, the insulating film sheet and the electrode base are both of transparent materials;
    the multi-modal sensor module is in a state of collecting electrocardiogram (ECG) signal, a side of the protective film away from the functional layer and a side of the electrode base away from the insulating film sheet are both for use in contacting surface of the biological tissues, so that the protective film, the biological tissues, and the electrode base form an ECG signal collection path;
    the multi-modal sensor module further comprising:
    a first wristband connected to the multi-modal sensor, a first temperature sensor module and a first bioimpedance sensor module; the first temperature sensor module surrounds a periphery of the electrode base, the first bioimpedance sensor module is provided at a side of the first wristband facing the biological tissues; and
    a second wristband, a second temperature sensor module and a second bioimpedance sensor module;
    wherein two ends of the second wristband are respectively connected with two ends of the electrode base; the second temperature sensor module is positioned at a side of the second wristband facing the biological tissues, the second bioimpedance sensor module is connected with the electrode base.

2. The multi-modal sensor module according to claim 1, wherein the sensor module comprises an ultrasonic sensor module; the ultrasonic sensor module comprises a plurality of piezoresistors arranged in an array; a side of the piezoresistors is arranged to face the protective film, and another side passes through the insulating film sheet and the electrode base for contacting surface of the biological tissues; a first portion of the piezoresistors is annularly distributed at an edge region of the substrate, a second portion of the piezoresistors is positioned at a center region of the substrate.

3. The multi-modal sensor module according to claim 2, wherein the sensor module further comprises a pressure sensor and an accelerometer; the pressure sensor and the accelerometer are positioned between the first portion of the piezoresistors and the second portion of the piezoresistors.

4. The multi-modal sensor module according to claim 3, wherein the sensor module further comprises a first photoplethysmography (PPG) sensor module; the first PPG sensor module comprises a light source, an optical barrier and a first photodetector arranged in interval in sequence; the light source, the optical barrier and the first photodetector are all positioned between the first portion of the piezoresistors and the second portion of the piezoresistors.

5. The multi-modal sensor module according to claim 4, wherein the light source comprises at least one monochromatic light source.

6. The multi-modal sensor module according to claim 1, wherein the sensor module further comprises a second PPG sensor module; the second PPG sensor module comprises at least two light sources and a second photodetector; the at least two light sources are evenly distributed at a periphery of the second photodetector.

7. The multi-modal sensor module according to claim 1, wherein the second bioimpedance sensor module comprises two voltage detecting electrode sheets and two electric current supplying electrode sheets; the electrode base comprises four holes; the two voltage detecting electrode sheets and the two electric current supplying electrode sheets are respectively embedded in the four holes, a side of the voltage detecting electrode sheets and the electric current supplying electrode sheets away from the protective film being flush with a side of the electrode base away from the insulating film sheet.

8. A multi-modal physiological signal monitoring system, comprising the multi-modal sensor module according to claim 1.

* * * * *